(12) United States Patent
Dahmen et al.

(10) Patent No.: US 12,357,762 B2
(45) Date of Patent: Jul. 15, 2025

(54) METERING MECHANISM AND INJECTION DEVICE

(71) Applicant: Sanofi-Aventis Deutschland GMBH, Frankfurt am Main (DE)

(72) Inventors: Michael Dahmen, Kronberg (DE); Hannes Obex, Dusseldorf (DE)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 847 days.

(21) Appl. No.: 17/270,177

(22) PCT Filed: Aug. 27, 2019

(86) PCT No.: PCT/EP2019/072760
§ 371 (c)(1),
(2) Date: Feb. 22, 2021

(87) PCT Pub. No.: WO2020/043686
PCT Pub. Date: Mar. 5, 2020

(65) Prior Publication Data
US 2021/0244891 A1    Aug. 12, 2021

(30) Foreign Application Priority Data
Aug. 29, 2018  (EP) .................................. 18191426

(51) Int. Cl.
*A61M 5/315*    (2006.01)
(52) U.S. Cl.
CPC .... *A61M 5/31541* (2013.01); *A61M 5/31551* (2013.01); *A61M 5/31585* (2013.01)
(58) Field of Classification Search
CPC .......... A61M 5/31541; A61M 5/31551; A61M 5/31583; A61M 5/31585; A61M 5/31501; A61M 5/31528; A61M 2005/3154
See application file for complete search history.

(56) References Cited

U.S. PATENT DOCUMENTS

| | | | |
|---|---|---|---|
| 2009/0275916 A1 | 11/2009 | Harms et al. | |
| 2011/0319835 A1* | 12/2011 | Burren | A61M 5/31551 604/209 |

(Continued)

FOREIGN PATENT DOCUMENTS

| | | |
|---|---|---|
| CN | 1723054 | 1/2006 |
| CN | 103313743 | 9/2013 |

(Continued)

OTHER PUBLICATIONS

PCT International Preliminary Report on Patentability in International Application No. PCT/EP2019/072760, dated Mar. 2, 2021, 7 pages.

(Continued)

*Primary Examiner* — Courtney B Fredrickson
*Assistant Examiner* — Kayla M. Turkowski
(74) *Attorney, Agent, or Firm* — Bond, Schoeneck & King, PLLC

(57) ABSTRACT

The present disclosure provides a metering mechanism for an injection device. The mechanism comprises an actuating element for setting or discharging a dose from the injection device, a piston rod for producing an advance movement for dispensing a dose, a piston rod sleeve in which the piston rod is accommodated such that the piston rod can be non-rotatably connected to the piston rod sleeve, and a coupling element with which the actuating element and the piston rod sleeve can be coupled for discharge of the dose set with the actuating element. To prevent underdosage, the piston rod comprises a stop and the coupling element comprises a counter-stop which move relative to each other at least during setting of a dose and which abut each other in a maximum dose stop position, thereby preventing further setting of a dose.

19 Claims, 3 Drawing Sheets

(56) References Cited

U.S. PATENT DOCUMENTS

| | | | |
|---|---|---|---|
| 2016/0067414 A1* | 3/2016 | Bayer | A61M 5/31553 604/211 |
| 2016/0114108 A1* | 4/2016 | Bernert | A61M 5/31535 604/211 |
| 2016/0121052 A1 | 5/2016 | Burren et al. | |

FOREIGN PATENT DOCUMENTS

| | | |
|---|---|---|
| EP | 0474839 | 9/1994 |
| EP | 2643036 | 11/2017 |
| EP | 3299052 | 3/2018 |
| JP | 2006-501036 | 1/2006 |
| JP | 2011-519600 | 7/2011 |
| JP | 2013-532569 | 8/2013 |
| WO | WO 2004/030730 | 4/2004 |
| WO | WO 2009/132778 | 11/2009 |
| WO | WO 2012/017036 | 2/2012 |
| WO | WO 2012/069085 | 5/2012 |
| WO | WO-2014191190 A1 * 12/2014 | A61M 5/20 |
| WO | WO-2018041899 A1 * 3/2018 | A61M 5/31526 |

OTHER PUBLICATIONS

PCT International Search Report and Written Opinion in International Application No. PCT/EP2019/072760, dated Oct. 11, 2019, 11 pages.

\* cited by examiner

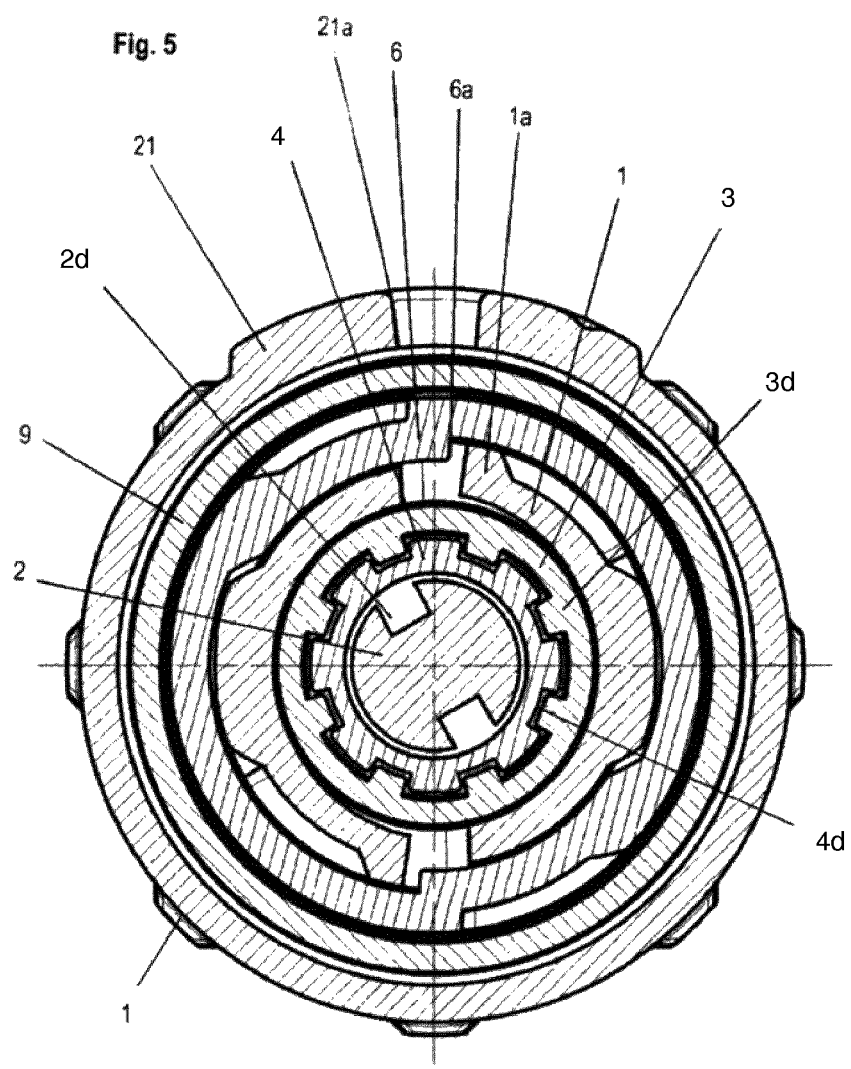

METERING MECHANISM AND INJECTION DEVICE

CROSS-REFERENCE TO RELATED APPLICATIONS

The present application is the national stage entry of International Patent Application No. PCT/EP2019/072760, filed on Aug. 27, 2019, and claims priority to Application No. EP 18191426.8, filed on Aug. 29, 2018, the disclosures of which are incorporated herein by reference.

TECHNICAL FIELD

The present disclosure is generally directed to a drug delivery device, e.g. an injection device for selecting and dispensing a number of user variable doses of a medicament. The disclosure is further directed to an improved metering mechanism for such an injection device.

BACKGROUND

Pen type drug delivery devices have application where regular injection by persons without formal medical training occurs. This may be increasingly common among patients having diabetes where self-treatment enables such patients to conduct effective management of their disease. In practice, such a drug delivery device allows a user to individually select and dispense a number of user variable doses of a medicament. The present disclosure is further directed to so called fixed dose devices which only allow dispensing of a predefined dose without the possibility to increase or decrease the set dose.

There are basically two types of drug delivery devices: resettable devices (i.e., reusable) and non-resettable (i.e., disposable). For example, disposable pen delivery devices are supplied as self-contained devices. Such self-contained devices do not have removable pre-filled cartridges. Rather, the pre-filled cartridges may not be removed and replaced from these devices without destroying the device itself. Consequently, such disposable devices need not have a resettable dose setting mechanism. The present disclosure is applicable for both types of devices, i.e. for disposable devices as well as for reusable devices.

These types of pen delivery devices (so named because they often resemble an enlarged fountain pen) generally comprise three primary elements: a cartridge section that includes a cartridge often contained within a housing or holder; a needle assembly connected to one end of the cartridge section; and a dosing section connected to the other end of the cartridge section. A cartridge (often referred to as an ampoule) typically includes a reservoir that is filled with a medication (e.g., insulin), a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The needle assembly is typically a replaceable double-ended needle assembly. Before an injection, a replaceable double-ended needle assembly is attached to one end of the cartridge assembly, a dose is set, and then the set dose is administered. Such removable needle assemblies may be threaded onto, or pushed (i.e., snapped) onto the pierceable seal end of the cartridge assembly.

The dosing section or dose setting mechanism is typically the portion of the pen device that is used to set (select) a dose. During an injection, a spindle or piston rod contained within the dose setting mechanism presses against the bung or stopper of the cartridge. This force causes the medication contained within the cartridge to be injected through an attached needle assembly. After an injection, as generally recommended by most drug delivery device and/or needle assembly manufacturers and suppliers, the needle assembly is removed and discarded.

A further differentiation of drug delivery device types refers to the drive mechanism: There are devices which are manually driven, e.g. by a user applying a force to an injection button, devices which are driven by a spring or the like and devices which combine these two concepts, i.e. spring assisted devices which still require a user to exert an injection force. The spring-type devices involve springs which are preloaded and springs which are loaded by the user during dose selecting. Some stored-energy devices use a combination of spring preload and additional energy provided by the user, for example during dose setting.

EP 2 643 036 B1 discloses a resettable injection device comprising a metering mechanism for selecting an individual dose to be discharged by the injection device. The set dose may be increased or decreased by operation of an actuating element which can also be used for discharging a dose from the injection device. A drawback of this metering mechanism is the lack of a safety feature preventing setting a dose which exceeds the dischargeable amount of liquid left in the cartridge. For example, if the cartridge is nearly empty a user is still allowed to set a dose significantly exceeding the dose which is present in the cartridge. If a user discharges this set dose there is a risk that the user assumes to have discharged a higher dose than the amount of medicament actually discharged from the injection device. This may result in a severe underdosage which may cause health problems.

Metering mechanisms for injection devices having a safety feature preventing setting of a dose which exceeds the dischargeable amount of liquid left in the cartridge are known for example from EP 0 474 839 B1 which discloses a mechanism having a pawl which moves on a helical path during dose setting and engages the recess in a plunger at a predefined position thereby preventing further rotation of the pawl and, thus, selecting a dose greater than remaining for dispensing within the cartridge.

SUMMARY

The present disclosure relates to an improved metering mechanism with such a safety feature and an injection device with such a metering mechanism.

This object is solved by a metering mechanism as defined in claim 1 and an injection device as defined in claim 14.

A metering mechanism preferably comprises an actuating element for setting or discharging a dose from the injection device, a piston rod for producing an advance movement for dispensing a dose, a piston rod sleeve in which the piston rod is accommodated such that the piston rod can be non-rotatably connected to the piston rod sleeve, a coupling element with which the actuating element and the piston rod sleeve can be coupled for discharge of the dose set with the actuating element in such a way that a dispensing movement of the actuating element is transmitted to the piston rod by way of the piston rod sleeve connected to the piston rod and a reverse rotation prevention element for the piston rod sleeve, to permit rotation of the piston rod sleeve in one direction and to block it in the opposite direction. According to the present disclosure the mechanism further comprises a limiter for limiting the maximum dose to be set by means of the actuating element. In more detail, the limiter may limit the maximum dose which can be individually set by a user or, preferably, the limiter may prevent setting of a dose which exceeds the dischargeable amount of liquid left in a cartridge of an injection device. An example of present disclosure uses the piston rod and the coupling element for such a limiter.

In an embodiment of the present disclosure the piston rod comprises a stop and the coupling element comprises a counter-stop which move relative to each other at least during setting of a dose and which abut each other in a maximum dose stop position, thereby preventing further setting of a dose. This includes embodiments where the stop and the counter-stop move relative to each other during discharging of a set dose, too. For example, the stop and the counter-stop may move away from each other a small distance during discharging of a set dose, while moving towards each other a larger distance during dose setting. This may correspond to the coupling element performing a relatively large stroke during dose setting and dose discharging, while the piston rod performs only a relatively small stroke during dose discharging (and remains stationary during dose setting). Such different strokes generate a mechanical advantage similar to a gearing for reducing the force the user has to apply during dose discharging.

Relative movement between the stop of the piston rod and the counter-stop of the coupling element during setting of a dose may be achieved by a reverse rotation prevention element which is rotationally constrained to the housing and prevents rotation and, thus, axial movement of the piston rod and by coupling the coupling element to the actuating element such that an axial or helical dose setting movement of the actuating element entrains the coupling element in an axial direction. In other words, the piston rod may be held stationary during dose setting by means of the reverse rotation prevention element whereas the coupling element is moved axially during dose setting by means of the actuating element. Preferably, the coupling element comprises a tubular portion guided within the piston rod sleeve. The coupling element may be rotationally constrained to the piston rod sleeve by means of the tubular portion.

For example, in an embodiment of the metering mechanism the coupling element comprises a tubular portion guided within the piston rod sleeve wherein the piston rod comprises a stop and the coupling element comprises a counter-stop which move relative to each other at least during setting of a dose and which abut each other in a maximum dose stop position, thereby preventing further setting of a dose, wherein the stop remains stationary during setting of a dose and the stop and the counter-stop move axially towards each other during setting of a dose.

The stop may be a radial protrusion integrally formed on the piston rod, for example in the form of a radially outwards protruding flange or in the form of a bulkhead. Preferably, the stop is located at or near the proximal end of the piston rod, i.e. the end facing away from the needle side of the injection device. The counter-stop may be a radial protrusion integrally formed on the coupling element, for example in the form of a radially inwards protruding flange. Preferably, the counter-stop is located at or near the distal end of the coupling element, i.e. the end facing towards the needle side of the injection device.

The limiter of the metering mechanism requires a relative movement of the stop and the counter-stop during setting of a dose. Preferably, the stop and to the counter-stop move axially towards each other. This includes embodiments wherein the stop and/or the counter-stop performs a combined axial and rotational movement, for example along a helical path. In a preferred embodiment of the present disclosure the stop remains stationary during dose setting and the counter-stop performs a pure linear movement in the proximal direction towards the stop during dose setting. In addition or as an alternative, the stop and the counter-stop may both move on a respective helical path in the same direction during dose discharging. For example, the pitch of the helical path of the stop may be smaller than the pitch of the helical path of the counter-stop.

If dose setting is stopped by the limiter, i.e. by abutment of the stop and the counter-stop, discharging of the (limited) set dose may be desirable. For this purpose the metering mechanism may be designed such that upon abutment of the stop and the counter-stop further axial displacement of the coupling element in a direction increasing the dose set with the actuating element is prevented, whereas the dispensing movement of the actuating element and a respective movement of the piston rod is permitted.

According to a further embodiment the piston rod may be non-rotatably connected to the piston rod sleeve by means of a coupling sleeve wherein the coupling sleeve can be in engagement with the piston rod sleeve to form a non-rotatable connection between the piston rod and the coupling sleeve and wherein the coupling sleeve can be out of engagement with the piston rod sleeve such that the piston rod is rotatable relative to the piston rod sleeve. With this arrangement resetting of the piston rod is possible if an empty cartridge is to be replaced by a new cartridge in the reusable (resettable) injection device. For resetting the metering mechanism the piston rod may be axially displaceable relative to the piston rod sleeve when the coupling sleeve is out of engagement with the piston rod.

The actuating element may be coupled to the coupling element such that an axial movement of the actuating element for setting a dose is transmitted to the coupling element. For example, the coupling element may be entrained by the actuating element during dose setting. In addition or as an alternative, the actuating element may be coupled to the coupling elements such that the rotational movement of the actuating element for discharging a dose, e.g. a movement along a helical path, is transmitted to the coupling element. Further, the coupling element may have a coupling member and the actuating element may have a counterpart coupling member which can be coupled or opened relative to each other by an axial or radial displacement of the coupling element relative to the actuating element. For example, the actuating element may comprise a shoulder as the counterpart coupling member and the coupling element may comprise a flange as the coupling member arranged such that an axial movement of the actuating element for setting a dose is transmitted to the coupling element. The coupling member and the counterpart coupling member may each be provided with teeth adapted to engage and disengage for coupling and decoupling, respectively.

According to a further aspect of the present disclosure, the coupling element may comprise a tubular portion guided within the piston rod sleeve, wherein the tubular portion of the coupling element and the piston rod sleeve may comprise splines or the like preventing relative rotation of the coupling element and the piston rod sleeve and permitting relative axial displacement of the coupling element and the piston rod sleeve.

The reverse rotation prevention element of the metering mechanism and the piston rod sleeve may be in engagement by means of a tooth means or a latching means. For example, the reverse rotation prevention element has a spring arm or is in the form of a spring arm. Further, the reverse rotation prevention element and the piston rod sleeve may be coupled to each other. The reverse rotation prevention element is e.g. non-rotatably and axially fixedly connected to a housing of the metering mechanism.

The present disclosure further refers to an injection device having a metering mechanism as described above and comprising a cartridge holder for receiving a cartridge containing a medicament.

In the injection device, the stop and the counter-stop are preferably arranged adapted to the content of the cartridge such that the stop and the counter-stop abut each other if the dose set with the actuating element substantially corresponds to the remaining dischargeable content of the cartridge. For safety reasons it is more important to prevent that a user sets a dose which cannot be fully discharged from the cartridge than making sure that it is possible to empty the cartridge completely. In other words, the limiter according to the present disclosure may come into effect by abutment of the stop and the counter-stop in a situation where it would be theoretically possible to discharge a slightly larger amount of medicament from the cartridge than the actually set dose. This may include cases in which after discharging the dose limited by abutment of the stop and the counter-stop setting and/or discharging of a dose smaller than the dose limited by abutment of the stop and the counter-stop remains possible.

For resettable injection devices it is very convenient for the user if the coupling sleeve is brought in engagement with the piston rod sleeve by attachment of the cartridge holder to the injection device or a housing component thereof and if the coupling sleeve is brought out of engagement with the piston rod sleeve by detachment of the cartridge holder. This may be achieved for example as described in EP 2 643 036 B1.

The injection device typically comprises a cartridge containing a medicament. The term "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly (A21), Arg (B31), Arg (B32) human insulin; Lys (B3), Glu (B29) human insulin; Lys (B28), Pro (B29) human insulin; Asp (B28) human insulin; human insulin, wherein proline in position B28 is replaced by Asp, Lys, Leu, Val or Ala and wherein in position B29 Lys may be replaced by Pro; Ala (B26) human insulin; Des (B28-B30) human insulin; Des (B27) human insulin and Des (B30) human insulin.

Insulin derivates are for example B29-N-myristoyl-des (B30) human insulin; B29-N-palmitoyl-des (B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des (B30) human insulin; B29-N—(N-lithocholyl-Y-glutamyl)-des (B30) human insulin; B29-N-(ω-carboxyheptadecanoyl)-des (B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28]Exendin-4(1-39),
des Pro36 [IsoAsp28]Exendin-4(1-39),
des Pro36 [Met(O)14, Asp28]Exendin-4(1-39),
des Pro36 [Met(O)14, IsoAsp28]Exendin-4(1-39),
des Pro36 [Trp(O2)25, Asp28]Exendin-4(1-39),
des Pro36 [Trp(O2)25, IsoAsp28]Exendin-4(1-39),
des Pro36 [Met(O)14 Trp(O2)25, Asp28]Exendin-4(1-39),
des Pro36 [Met(O)14 Trp(O2)25, IsoAsp28]Exendin-4(1-39); or
des Pro36 [Asp28]Exendin-4(1-39),
des Pro36 [IsoAsp28]Exendin-4(1-39),
des Pro36 [Met(O)14, Asp28]Exendin-4(1-39),
des Pro36 [Met(O)14, IsoAsp28]Exendin-4(1-39),
des Pro36 [Trp(O2)25, Asp28]Exendin-4(1-39),
des Pro36 [Trp(O2)25, IsoAsp28]Exendin-4(1-39),
des Pro36 [Met(O)14 Trp(O2)25, Asp28]Exendin-4(1-39),
des Pro36 [Met(O)14 Trp(O2)25, IsoAsp28]Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28]Exendin-4(1-39)-Lys6-NH2,
des Asp28 Pro36, Pro37, Pro38Exendin-4(1-39)-NH2,
H-(Lys)6-des Pro36, Pro38 [Asp28]Exendin-4(1-39)-NH2,
H-Asn-(Glu)5des Pro36, Pro37, Pro38 [Asp28]Exendin-4(1-39)-NH2,
des Pro36, Pro37, Pro38 [Asp28]Exendin-4(1-39)-(Lys)6-NH2,
H-(Lys)6-des Pro36, Pro37, Pro38 [Asp28]Exendin-4(1-39)-(Lys)6-NH2,
H-Asn-(Glu)5-des Pro36, Pro37, Pro38 [Asp28]Exendin-4(1-39)-(Lys)6-NH2,
H-(Lys)6-des Pro36 [Trp(O2)25, Asp28]Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28]Exendin-4(1-39)-NH2, des Pro36, Pro37, Pro38 [Trp(O2)25, Asp28]Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28]Exendin-4(1-39)-(Lys)6-NH2, H-(Lys)6-des Pro36 [Met(O)14, Asp28]Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28]Exendin-4(1-39)-NH2, H-Asn-(Glu)5-des Pro36, Pro37, Pro38 [Met(O)14, Asp28]Exendin-4(1-39)-NH2, des Pro36, Pro37, Pro38 [Met(O)14, Asp28]Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28]Exendin-4(1-39)-(Lys)6-NH2, H-Lys6-des Pro36 [Met(O)14, Trp(O2)25, Asp28]Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28]Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28]Exendin-4 (S1-39)-(Lys)6-NH2, H-Asn-(Glu)5-des Pro36, Pro37, Pro38 [Met(O)14, Trp(O2)25, Asp28]Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains.

These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H-H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+ (R1) (R2) (R3) (R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Non-limiting, exemplary embodiments of the invention will now be described with reference to the accompanying drawings, in which:

BRIEF DESCRIPTION OF THE FIGURES

FIG. 5 schematically shows a further sectional view of an embodiment of an injection device with the metering mechanism of FIG. 2.

DETAILED DESCRIPTION

Figure 1:
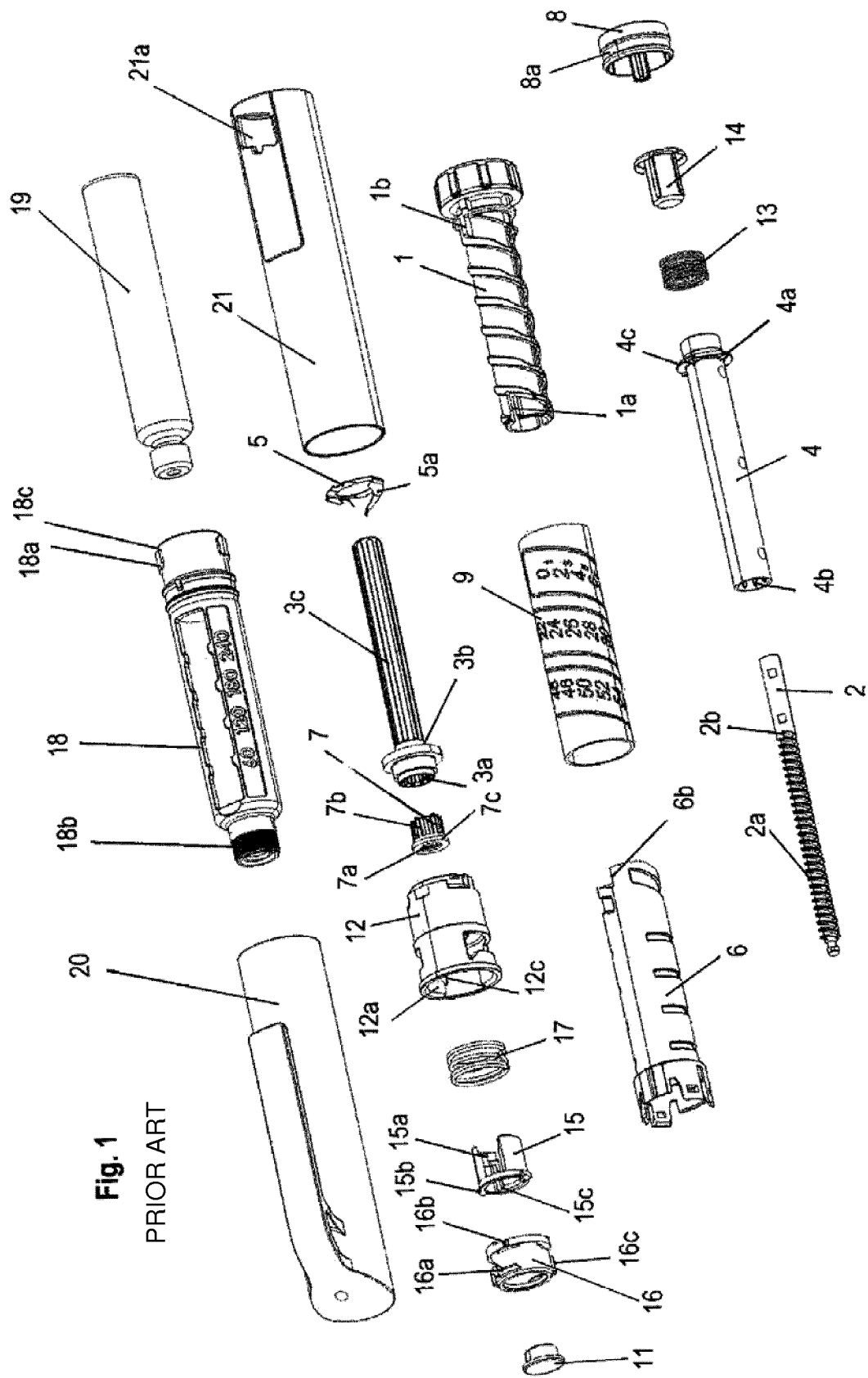
FIG. 1 schematically shows an injection device according to the prior art.

Referring to FIG. 1, there is shown an injection device as disclosed in EP 2 643 036 B1 with a metering mechanism. The metering mechanism comprises an actuating element 1 for setting and delivering a dose. The actuating element 1 has an external thread 1b, which is guided into an internal thread of an internal housing 6 of the metering mechanism. To set a dose, the actuating element 1 is screwed out of the housing 6 while the actuating element 1 is screwed back into the housing 6 to deliver (discharge) a dose. A number sleeve 9 (display sleeve) is arranged axially and rotationally fixed on the actuating element 1, to display the actually set dose in a display window 21a of an outer housing sleeve 21 which coaxially surrounds the housing 6. At a distal end of the external thread 1b, there is a stop cam 1a cooperating with a corresponding counter cam 6a (shown in FIG. 5) of the housing 6 to limit the setting of a maximum dose. In stop contact, the actuating element 1 cannot be unscrewed further out of the housing 6. A further stop cam 6b is provided as a minimum dose stop, typically preventing setting a dose below the dose value zero.

In the metering mechanism, a piston rod 2 is movably mounted with an external thread 2a for generating a movement for dispensing a dose. At the distal end of the piston rod 2, a pressure foot or flange 11 is rotatably arranged. During the advancing movement of the piston rod 2, the flange 11 abuts a rubber bung, which is movably received in a cartridge 19 in order to deliver a medicament from the injection device. The cartridge 19 is received in a cartridge holder 18. A detachable protective cap 20 is provided for receiving the cartridge holder 18.

The external thread 2a of the piston rod 2 is in a threaded engagement with an internal thread of a threaded sleeve 12. The threaded sleeve 12 is axially and rotatably constrained to the housing 6 via the outer housing sleeve 21. The threaded sleeve 12 serves to transform a rotational movement of the piston rod 2 in a combined rotational and axial movement of the piston rod 2. A stop cam 2b of the piston rod 2 can come into abutment contact with the threaded sleeve 12 when the cartridge 19 is empty. The distal end of the cartridge holder 18 has a thread 18b to connect a needle unit to the cartridge 19. At the proximal end of the cartridge holder 18 there is an outwardly projecting locking cam 18a which can be brought into engagement with a guide 12a in the threaded sleeve 12 to form a bayonet locking.

A piston rod sleeve 3 surrounds the piston rod 2 coaxially. A coupling sleeve 7 is provided for coupling the piston rod 2 detachably with the piston rod sleeve 3. For this purpose, the coupling sleeve 7 is rotationally constrained to the piston rod 2, for example by means of a rib 7a provided on an inner surface of the coupling sleeve 7 engaging a longitudinally extending groove 2d (see FIG. 5) of the piston rod 2. Further, longitudinally extending ribs 7b are arranged on an outer surface of the coupling sleeve 7 which engage grooves 3a on an inner surface of the piston rod sleeve 3.

A coupling element 4 is provided for coupling the actuating element 1 and the piston rod sleeve 3 such that a dose discharging movement of the actuating element 1 can be transmitted to the piston rod 2 via the piston rod sleeve 3 and the coupling sleeve 7. Longitudinally extending ribs 4b are arranged on an inner surface of the coupling element 4 which engage corresponding ribs 3c extending on an outer surface of the piston rod sleeve 3 to provide a rotationally fixed connection between the coupling element 4 and the piston rod sleeve 3. However, due to the rib connection, the coupling element 4 can move axially relative to the piston rod sleeve 3. The coupling element 4 is provided with a coupling element 4a in the form of a flange with a tooth 4c which can engage with a corresponding coupling element, e.g. a ring of teeth (not shown), arranged on an internal shoulder of the actuating element 1.

A knob 8 is rotatably mounted in the actuating element 1 by means of a snap connection 8a. A spring 13 is disposed within the knob 8 and is supported at the distal end on a flange 4a of the coupling element 4 and at the proximal end on a spring holder 14 which is held in the knob 8.

The metering mechanism further comprises a reverse rotation prevention element 5 with a spring arm 5a. The reverse rotation prevention element 5 is rotationally and axially fixed to the housing 6. The spring arm 5a engages a toothing 3b on a radially protruding flange of the piston rod sleeve. The spring arm 5a and the toothing 3b are designed such that the piston rod sleeve 3 can only be rotated in one direction relative to the spring arm 5a, namely during dose discharging.

The coupling sleeve 7, a coupling ring 15, a coupling holder 16 and a clutch spring 17 are mounted in the threaded sleeve 12. At its distal end, the coupling sleeve 7 has an outwardly projecting ring 7c. The coupling ring 15 comprises webs extending in the longitudinal direction which are provided with an annular groove 15a. The ring 7c of the coupling sleeve 7 is axially fixed in the annular groove 15a but free to rotate with respect to the coupling ring 15. A guide cam 15b is arranged at the distal end of the coupling ring 15 for engaging a guide track 16a of the coupling holder 16. The guide track 16a is designed such that the guide cam 15b can be guided with respect to the threaded sleeve 12 during rotation of the coupling ring 15.

The clutch spring 17 is supported at its proximal end on the threaded sleeve 12 and with its distal end on the coupling holder 16. The coupling holder 16 is axially displaceable and rotatable relative to the threaded sleeve 12, whereas the coupling ring 15 is axially movable but rotationally fixed with respect to the threaded sleeve 12. The cartridge holder 18 has a recess 18c which can engage with a cam 16c of the coupling holder 16. The coupling holder 16 has a projection 16b to be guided in the threaded sleeve for attaching the coupling holder 16 with a cartridge holder 18 in a locking position. An inwardly projecting web 15c is mounted on an inner surface of the coupling ring 15 which is received in a longitudinal groove 12c of the threaded sleeve 12. Due to the guide slot between the coupling holder 16 and the coupling ring 15, a rotation of the coupling holder 16 relative to the threaded sleeve 12 results in an axial movement of the coupling ring 15 (with coupling sleeve 7) relative to the threaded sleeve 12, thereby bringing coupling sleeve 7 in an out of engagement with the piston rod sleeve 3 depending on the direction of rotation of the coupling holder, i.e. depending of attachment or detachment of the cartridge holder 18.

In order to set the dose with the injection device of FIG. 1, a user rotates actuating element 1 in a first direction such that the actuating element 1 winds out of housing 6 and housing sleeve 21 guided by external thread 1b. Coupling element 4 is axially entrained by actuating element 1 with flange 4a abutting a respective shoulder in actuating element 1. Tooth 4c rides over the teeth in actuating element 1 compressing spring 13. Due to the splined engagement of the coupling element 4 with the piston rod sleeve 3 the coupling element 4 is prevented from rotation by means of reverse rotation prevention element 5 acting on piston rod sleeve 3. With the cartridge holder 18 attached to the threaded sleeve 12, coupling sleeve 7 and engages piston rod sleeve 3 such that the piston rod 2 is prevented from rotating, too. During dose setting a respective dose value printed on the number sleeve 9 is displayed in the window 21a as of the number sleeve 9 rotates together with actuating element 1.

After a dose has been set, the user may discharge the dose by pushing on knob 8. This compresses spring 13 such that tooth 4c is kept in engagement with the respective teeth of actuating element 1. Further, actuating element 1 is wound back into the housing 6 and housing sleeve 21, wherein rotation of the actuating element 1 is transmitted via the coupling element 4 to the piston rod sleeve 3 and, thus, via coupling sleeve 7 to piston rod 2. Due to the threaded engagement of the piston rod 2 with the threaded sleeve 12, the piston rod 2 translates axially in the distal direction with the flange 11 acting on a bung (not shown) in the cartridge 19.

With respect to further details of the dose setting and dose discharging operation as well as to exchanging the cartridge 19 and resetting piston rod 2 reference is made to EP 2 643 036 B1.

Turning now to FIGS. 2 to 5 an embodiment of the present disclosure is described which is based on the injection device as mentioned above and as disclosed in EP 2 643 036 B1. Like reference numerals are used for components corresponding to components described above with respect to FIG. 1.

Figure 2:
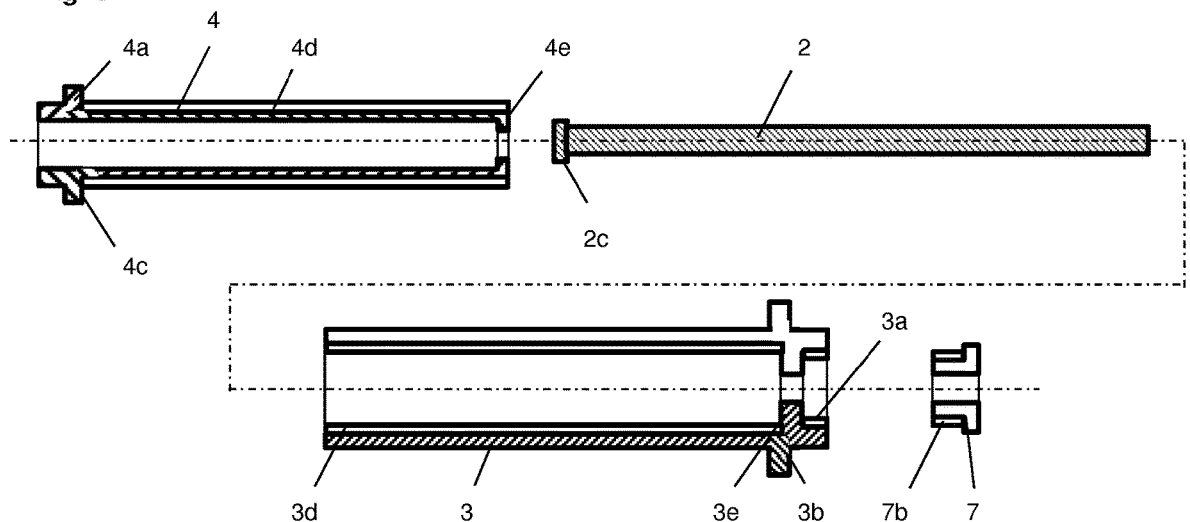
FIG. 2 schematically shows an exploded sectional view of component parts of a metering mechanism according to an embodiment of the present disclosure.

As can be taken from FIG. 2 the piston rod 2 is amended with respect to the piston rod of FIG. 1 in that a flange like stop 2c is provided at the proximal end of the piston rod 2. The position of the stop 2c is chosen such that the stop 2c reaches a distal portion of the piston rod sleeve when the cartridge 19 is nearly empty. The piston rod is an elongate member with an outer thread 2a which is not shown in FIGS. 2 to 5.

The piston rod sleeve 3 and to the coupling element 4 are both elongate tubular elements which are guided in each other. The coupling element 4 has a tubular portion guided within the piston rod sleeve 3. The piston rod sleeve 3 and the coupling element 4 are amended with respect to FIG. 1 in that the coupling element 4 has a reduced diameter and is arranged within the piston rod sleeve 3 which has an increased diameter. The piston rod sleeve 3 and the coupling element 4 are rotationally constrained to each other by means of external grooves 4d (between ribs) of the coupling element 4 and internal ribs 3d of the piston rod sleeve 3. Relative axial movement between the piston rod sleeve 3 and the coupling element 4 remains possible. A counter-stop 4e is provided at the distal end of coupling element 4 in the form of a radially inwards protruding flange. The length of the coupling element and the position of counter-stop 4e is chosen such that the counter-stop 4e may come in contact with stop 2c when the cartridge 19 is nearly empty but does not interfere with stop 2c when the cartridge 19 is substantially full, i.e. as long as the piston rod 2 is not displaced distally too far.

Figure 3:
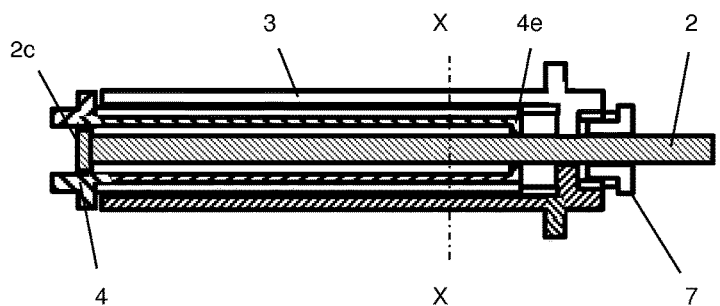
FIG. 3 schematically shows a sectional view of the metering mechanism of FIG. 2 in a state permitting setting a dose.
Figure 4:
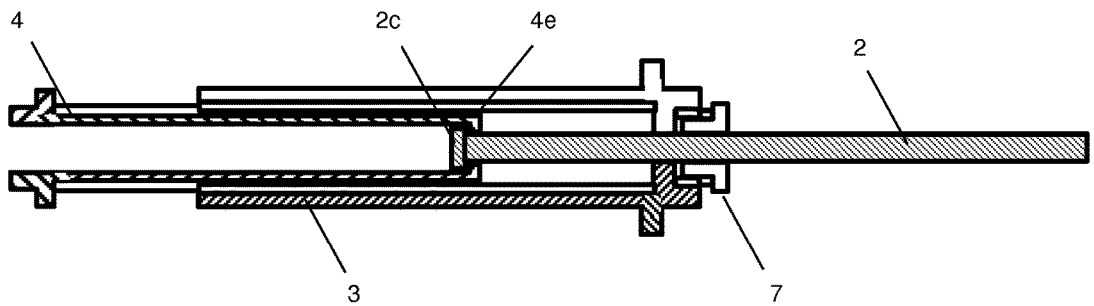
FIG. 4 schematically shows a sectional view of the metering mechanism of FIG. 2 in a state preventing setting a dose.

In the exemplary embodiment depicted in FIGS. 2 to 4 the piston rod sleeve 3 is provided with an optional inwardly protruding flange 3e forming a guiding portion for of the piston rod 2. With the piston rod 2 being guided in the threaded sleeve 12, in the coupling sleeve 7 and, optionally, in counter-stop 4e of the coupling element 4, the protruding flange 3e may be omitted. The metering mechanism may comprise in addition to the piston rod 2, the piston rod sleeve 3, the coupling element 4 and the coupling sleeve 7 depicted in FIGS. 2 to 4 an actuating element as shown in FIG. 1 and a reverse rotation prevention element as shown in FIG. 1.

As an alternative to the reverse rotation prevention element 5 shown in FIG. 1, the reverse rotation prevention element may be designed as comprising an, e.g. circumferentially extending, ratchet arm provided on or near the distal flange of the piston rod sleeve 3 wherein the toothing 3b on this flange might be omitted. Such a ratchet arm may interact with teeth or ribs on the inner surface of housing 6 such that rotation of the piston rod sleeve 3 is permitted in one direction (dose discharging) and is blocked in the opposite direction. Further alternatives to the reverse rotation prevention element 5 shown in FIG. 1 may include a ratchet arm provided as an integral part of housing 6 acting on teeth or ribs provided on the piston rod sleeve 3, e.g. on the distal flange.

In the example depicted in FIG. 1, the coupling sleeve 7 is splined to the piston rod 2 and in threaded engagement with the threaded sleeve 12. As an alternative, the coupling sleeve 7 may be provided with an internal thread engaging the external thread 2a of the piston rod 2 while the piston rod 2 is in splined engagement with sleeve 12 such that rotation of the piston rod 2 with respect to sleeve 12 is prevented but axial displacement of the piston rod 2 with respect to sleeve 12 is permitted. This would result in the piston rod 2 being displaced without rotation when discharging a dose.

FIG. 3 shows the metering mechanism in a state in which the piston rod 2 is in a retracted (proximal) position such that stop 2c is axially spaced from counter-stop 4e. When a dose is set, e.g. by rotating an actuating element coupled to the coupling element 4, the coupling element 4 is retracted in the proximal direction with respect to piston rod 2 which remains stationary together with piston rod sleeve 3 during dose setting. Rotation of the piston rod sleeve 3 and the piston rod 2 are prevented by the reverse rotation prevention element. The relative axial movement of the coupling element 4 with respect to the piston rod sleeve 3 results in the counter-stop 4e moving axially in the direction towards the stop 2c during dose setting. However, with the piston rod 2 being in its retracted (proximal) position stop 2c does not interfere with counter-stop 4e during dose setting (dose increasing).

FIG. 4 shows the metering mechanism after several doses have been discharged such that the piston rod 2 with stop 2c is displaced in the distal direction compared to the state depicted in FIG. 3. In addition, a dose is set in the state depicted in FIG. 4 as can be seen from the proximal displacement of the coupling element 4 with counter-stop 4e relative to the piston rod sleeve 3. This is a maximum dose stop position.

In FIG. 4 the dose set substantially corresponds to the dischargeable amount of medicament in the cartridge 19. In this situation stop 2c abuts counter-stop 4e, thereby preventing further proximal movement of the coupling element 4 with respect to the piston rod 2. As the piston rod 2 is prevented from being retracted in the proximal direction due to the reverse rotation prevention element acting on piston rod sleeve 3, further proximal movement of the coupling element 4 is stopped by this abutment. This results in stopping the dose setting movement of the actuating element which is in axial engagement with the coupling element 4 by means of flange 4c. In other words, stop 2c and counter-stop 4e form a limiter preventing setting of a dose which exceeds the amount of medicament remaining in the cartridge 19.

In the state depicted in FIG. 4 the set dose can be discharged from the injection device as explained above with respect to FIG. 1 by winding the actuating element back into the mechanism while engaging the coupling between the actuating element and the coupling element 4. This results in a common rotation of the actuating element, the coupling element 4, the piston rod sleeve 3, the coupling sleeve 7 and the piston rod 2. Due to the threaded engagement of the piston rod 2 with the threaded sleeve 12, this rotation drives the piston rod 2 in the distal direction with respect to the threaded sleeve 12 and the piston rod sleeve 3. However, in the state depicted in FIG. 4, it is impossible to increase the set dose. This prevents the risk of an underdosage.

After discharging the (limited) dose the cartridge 19 may be replaced by the full cartridge if the injection device is a resettable injection device. For this purpose of the cartridge holder 18 is a detached from the threaded sleeve 12 which decouples coupling sleeve 7 from piston rod sleeve 3 as explained in more detail in EP 2 643 036 B1 due to interaction with coupling ring 16 and coupling holder 15. The piston rod 2 can then be pushed back into the position depicted in FIG. 3 guided within the coupling sleeve 7 but without transmitting the rotation of the piston rod 2 to the piston rod sleeve 3. When pushing back the piston rod 2, the stop 2c translates away from the counter-stop 4e, thus again permitting dose setting for the new cartridge.

FIG. 5 schematically shows a metering mechanism similar to that of FIGS. 2 to 4 implemented into the injection device of FIG. 1 in a sectional view along line X-X in FIG. 3. While the general design and arrangement of the component parts as well as in their interaction is identical to the embodiment depicted in FIGS. 2 to 4, the dimensions of the component parts of the metering mechanism shown in FIG. 5 slightly differs from FIGS. 2 to 4. FIG. 5 shows a groove 2d engaging rib 7a (not shown in FIG. 5) for providing a rotationally fixed guiding of the piston rod 2 in the coupling sleeve 7.

There metering mechanism with the limiter according to the present disclosure may be used in resettable (i.e., reusable) devices and in non-resettable (i.e., disposable) devices. Further, the limiter may be used not only in manually driven injection devices as explained with respect to FIGS. 1 to 5 but also in spring driven or spring assisted devices.

| Reference Numerals | | | |
|---|---|---|---|
| 1 | actuating element | 7c | ring |
| 1a | cam | 8 | knob |
| 1b | outer thread | 8a | snap feature |
| 2 | piston rod | 9 | number sleeve |
| 2a | outer thread | 11 | flange |
| 2b | cam | 12 | threaded sleeve |
| 2c | stop | 12a | guide |
| 2d | groove | 12c | groove |
| 3 | piston rod sleeve | 13 | spring |
| 3a | grooves | 14 | spring holder |
| 3b | toothing | 15 | coupling ring |
| 3c | ribs | 15a | groove |
| 3d | ribs | 15b | cam |
| 3e | flange | 15c | web |
| 4 | coupling element | 16 | coupling holder |
| 4a | flange | 16a | guide track |
| 4b | ribs | 16b | projection |
| 4c | tooth | 16c | cam |
| 4d | groove | 17 | spring |
| 4e | counter-stop | 18 | cartridge holder |
| 5 | reverse rotation prevention element | 18a | cam |
| 5a | arm | 18b | thread |
| 6 | housing | 18c | recess |
| 6a | cam | 19 | cartridge |
| 6b | cam | 20 | cap |
| 7 | coupling sleeve | 21 | housing sleeve |
| 7a | rib | 21a | window |
| 7b | ribs | | |

The invention claimed is:

1. A metering mechanism for an injection device, comprising:
   an actuating element for setting or discharging a dose from the injection device;
   a piston rod for producing an advance movement for dispensing the dose;
   a piston rod sleeve in which the piston rod is accommodated such that the piston rod can have a rotationally locked connection with the piston rod sleeve;
   a coupling element to couple the actuating element with the piston rod sleeve for discharge of the dose set with the actuating element in such a way that a dispensing movement of the actuating element is transmitted to the piston rod by way of the piston rod sleeve having the rotationally locked connection with the piston rod during the dispensing movement, wherein the coupling element comprises a tubular portion guided within the piston rod sleeve and an outer circumferential surface of the tubular portion is axially movable along an inner circumferential surface of the piston rod sleeve;
   a reverse rotation prevention element that permits a rotation of the piston rod sleeve in one direction and blocks the rotation of the piston rod sleeve in an opposite direction; and
   a coupling sleeve that detachably connects the piston rod to the piston rod sleeve, wherein the coupling sleeve is configured to be engaged with the piston rod sleeve to form a non-rotatable connection between the piston rod and the coupling sleeve, and wherein the coupling sleeve is configured to be disengaged from the piston rod sleeve such that the piston rod is rotatable relative to the piston rod sleeve;

wherein the piston rod comprises a stop, and the coupling element comprises a counter-stop, the stop and the counter-stop are configured to move relative to each other at least during setting of the dose and abut each other in a maximum dose stop position to prevent further setting of the dose; and wherein the stop remains stationary with the piston rod sleeve during setting of the dose and the counter-stop moves axially toward the stop during setting of the dose.

2. The metering mechanism according to claim 1, wherein the stop is a radial protrusion integrally formed on the piston rod.

3. The metering mechanism according to claim 1, wherein the counter-stop is a radial protrusion integrally formed on the coupling element.

4. The metering mechanism according to claim 1, wherein an abutment of the stop with the counter-stop prevents further axial displacement of the coupling element in a direction that would increase the dose set with the actuating element and permits the dispensing movement of the actuating element.

5. The metering mechanism according to claim 1, wherein the actuating element is coupled to the coupling element such that an axial movement of the actuating element for setting the dose is transmitted to the coupling element.

6. The metering mechanism according to claim 1, wherein the coupling element has a coupling member, and the actuating element has a counterpart coupling member, the coupling member and the counterpart coupling member being configured to be coupled or opened relative to each other by an axial or radial displacement of the coupling element relative to the actuating element.

7. The metering mechanism according to claim 6, wherein the actuating element comprises a shoulder as the counterpart coupling member, and the coupling member comprises a flange with at least one tooth arranged such that an axial movement of the actuating element for setting the dose is transmitted to the coupling element.

8. The metering mechanism according to claim 6, wherein the coupling member and the counterpart coupling member are each provided with respective teeth.

9. The metering mechanism according to claim 1, wherein the tubular portion of the coupling element and the piston rod sleeve comprise respective ribs and grooves that prevent relative rotation of the coupling element and the piston rod sleeve and permit relative axial displacement of the coupling element and the piston rod sleeve.

10. The metering mechanism according to claim 1, wherein the reverse rotation prevention element and the piston rod sleeve are in engagement by at least a tooth or a latch, and wherein the reverse rotation prevention element comprises a spring arm or is in the form of a spring arm.

11. The metering mechanism according to claim 1, wherein the reverse rotation prevention element and the piston rod sleeve are coupled, and/or the reverse rotation prevention element is non-rotatably and axially fixedly connected to a housing of the metering mechanism.

12. The metering mechanism according to claim 1, wherein the piston rod is axially displaceable relative to the piston rod sleeve when the coupling sleeve is disengaged with the piston rod.

13. An injection device, comprising:
a metering mechanism comprising:
an actuating element for setting or discharging a dose from the injection device;
a piston rod for producing an advance movement for dispensing the dose;
a piston rod sleeve in which the piston rod is accommodated such that the piston rod can have a rotationally locked connection with the piston rod sleeve;
a coupling element to couple the actuating element with the piston rod sleeve for discharge of the dose set with the actuating element in such a way that a dispensing movement of the actuating element is transmitted to the piston rod by way of the piston rod sleeve having the rotationally locked connection with the piston rod during the dispensing movement, wherein the coupling element comprises a tubular portion guided within the piston rod sleeve and an outer circumferential surface of the tubular portion is axially movable along an inner circumferential surface of the piston rod sleeve;
a reverse rotation prevention element that permits a rotation of the piston rod sleeve in one direction and blocks the rotation of the piston rod sleeve in an opposite direction; and
a coupling sleeve that detachably connects the piston rod to the piston rod sleeve by the coupling sleeve, wherein the coupling sleeve is configured to be engaged with the piston rod sleeve to form a non-rotatable connection between the piston rod and the coupling sleeve, and wherein the coupling sleeve is configured to be disengaged from the piston rod sleeve such that the piston rod is rotatable relative to the piston rod sleeve;
wherein the piston rod comprises a stop, and the coupling element comprises a counter-stop, the stop and the counter-stop are configured to move relative to each other at least during setting of the dose and abut each other in a maximum dose stop position to prevent further setting of the dose; and
wherein the stop remains stationary with the piston rod sleeve during setting of the dose and the counter-stop moves axially towards the stop during setting of the dose; and
a cartridge holder for receiving a cartridge containing a medicament;
wherein the stop and the counter-stop are positioned according to an amount of a remaining dischargeable medicament in the cartridge such that the stop and the counter-stop abut each other if the dose set with the actuating element corresponds to the remaining dischargeable medicament in the cartridge.

14. The injection device according to claim 13, wherein the coupling sleeve is configured to be engaged with the piston rod sleeve by an attachment of the cartridge holder into the injection device, and wherein the coupling sleeve is configured to be disengaged from the piston rod sleeve by a detachment of the cartridge holder from the injection device.

15. The injection device according to claim 13, wherein the stop is a radial protrusion integrally formed on the piston rod.

16. The injection device according to claim 13, wherein the coupling element has a coupling member, and the actuating element has a counterpart coupling member, the coupling member and the counterpart coupling member being configured to be coupled or opened relative to each other by an axial or radial displacement of the coupling element relative to the actuating element.

17. The injection device according to claim 16, wherein the actuating element comprises a shoulder as the counterpart coupling member, and the coupling member comprises a flange with at least one tooth arranged such that an axial movement of the actuating element for setting the dose is transmitted to the coupling element.

18. The injection device according to claim 13, wherein the tubular portion of the coupling element and the piston rod sleeve comprise respective ribs and grooves that prevent relative rotation of the coupling element and the piston rod sleeve and permit relative axial displacement of the coupling element and the piston rod sleeve.

19. The injection device according to claim 13, wherein the piston rod is axially displaceable relative to the piston rod sleeve when the coupling sleeve is out of engagement with the piston rod.

* * * * *